United States Patent [19]

Østensen et al.

[11] Patent Number: 6,133,316
[45] Date of Patent: Oct. 17, 2000

[54] USE OF NITRIC OXIDE INHIBITORS FOR TREATING SIDE EFFECTS OF PARTICULATE DRUGS

[75] Inventors: Jonny Østensen; Anne Sønstevold, both of Oslo, Norway

[73] Assignee: Nycomed Imaging AS, Oslo, Norway

[21] Appl. No.: 09/318,803

[22] Filed: May 26, 1999

Related U.S. Application Data

[63] Continuation of application No. PCT/GB97/03239, Nov. 26, 1997.

[60] Provisional application No. 60/046,647, May 16, 1997.

[30] Foreign Application Priority Data

Nov. 26, 1996 [GB] United Kingdom .................... 9624540

[51] Int. Cl.$^7$ .................................................. A61K 31/195
[52] U.S. Cl. ............................................................. 514/565
[58] Field of Search ............................................. 514/565

[56] References Cited

U.S. PATENT DOCUMENTS 5,441,982  8/1995  Itzhak .

FOREIGN PATENT DOCUMENTS 91 04024  4/1991  WIPO .
95 09621  4/1995  WIPO .

OTHER PUBLICATIONS

Baile, Acad. Radiol., vol. 2, No. 11, 980–984 (1995).
Lasser, Invest. Radiol., vol. 29, No. supp. 2, s102–s104 (1994).
Lasser, Acad. Radiol., vol. 2, No. 7, 559–564 (1995).
Amir, Eur. J. Pharmacol., vol. 203, No. 1, 125–127 (1991).

*Primary Examiner*—William R. A. Jarvis
*Attorney, Agent, or Firm*—Bacon & Thomas

[57] ABSTRACT

The present invention describes the use of a nitric oxide synthetase inhibitor or nitric oxide antagonist to reduce or eliminate unwanted physiological effects encountered with the parenteral administration of particulate drugs.

21 Claims, 7 Drawing Sheets

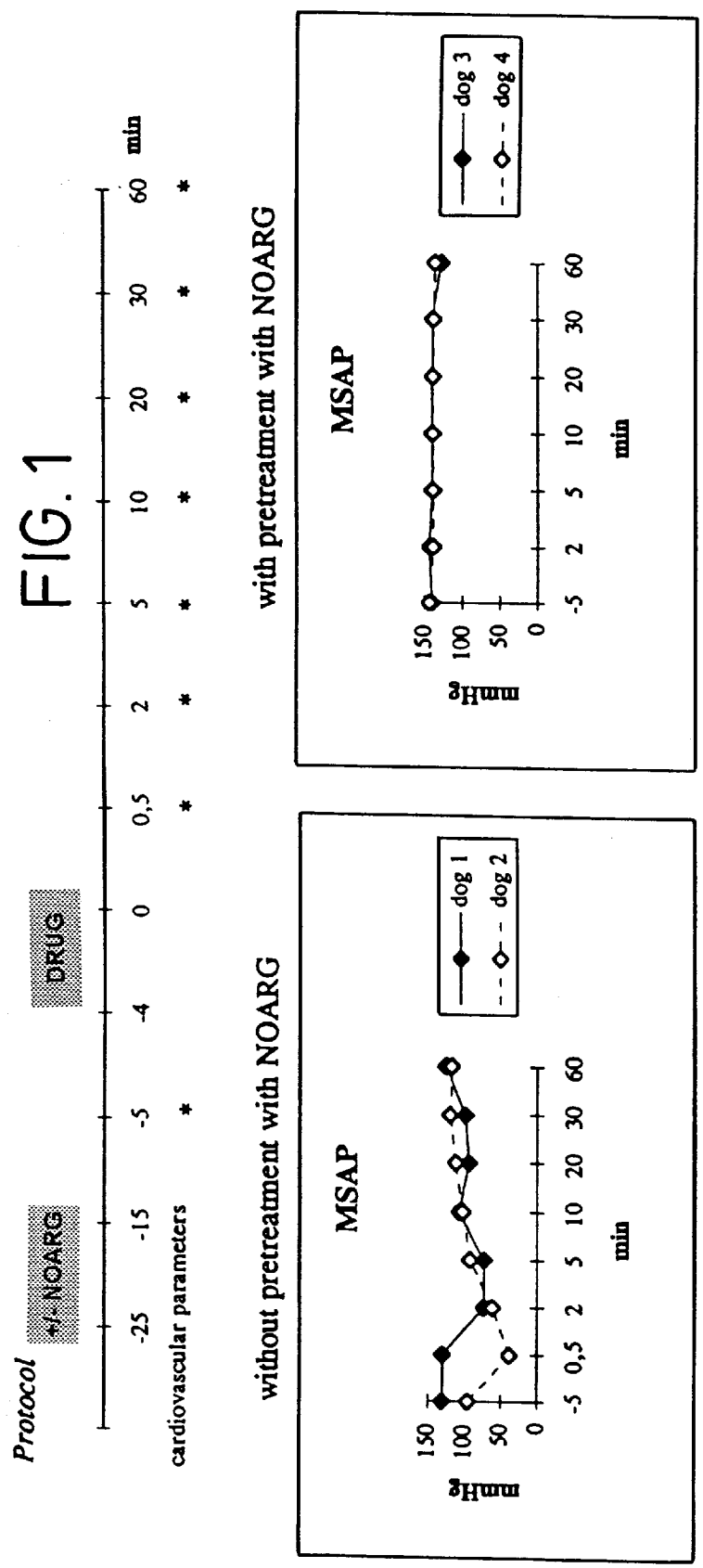

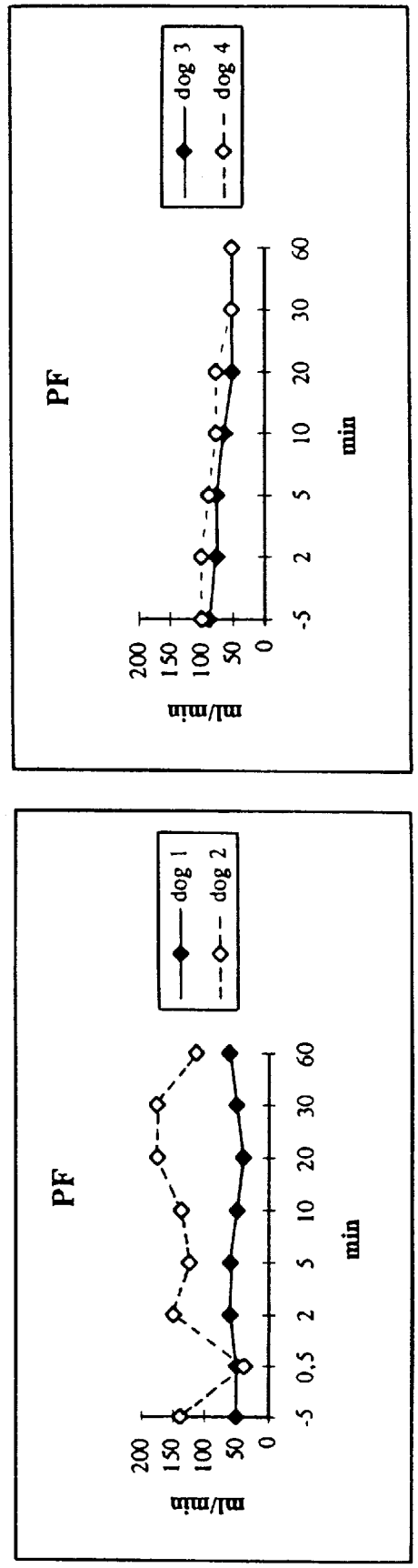

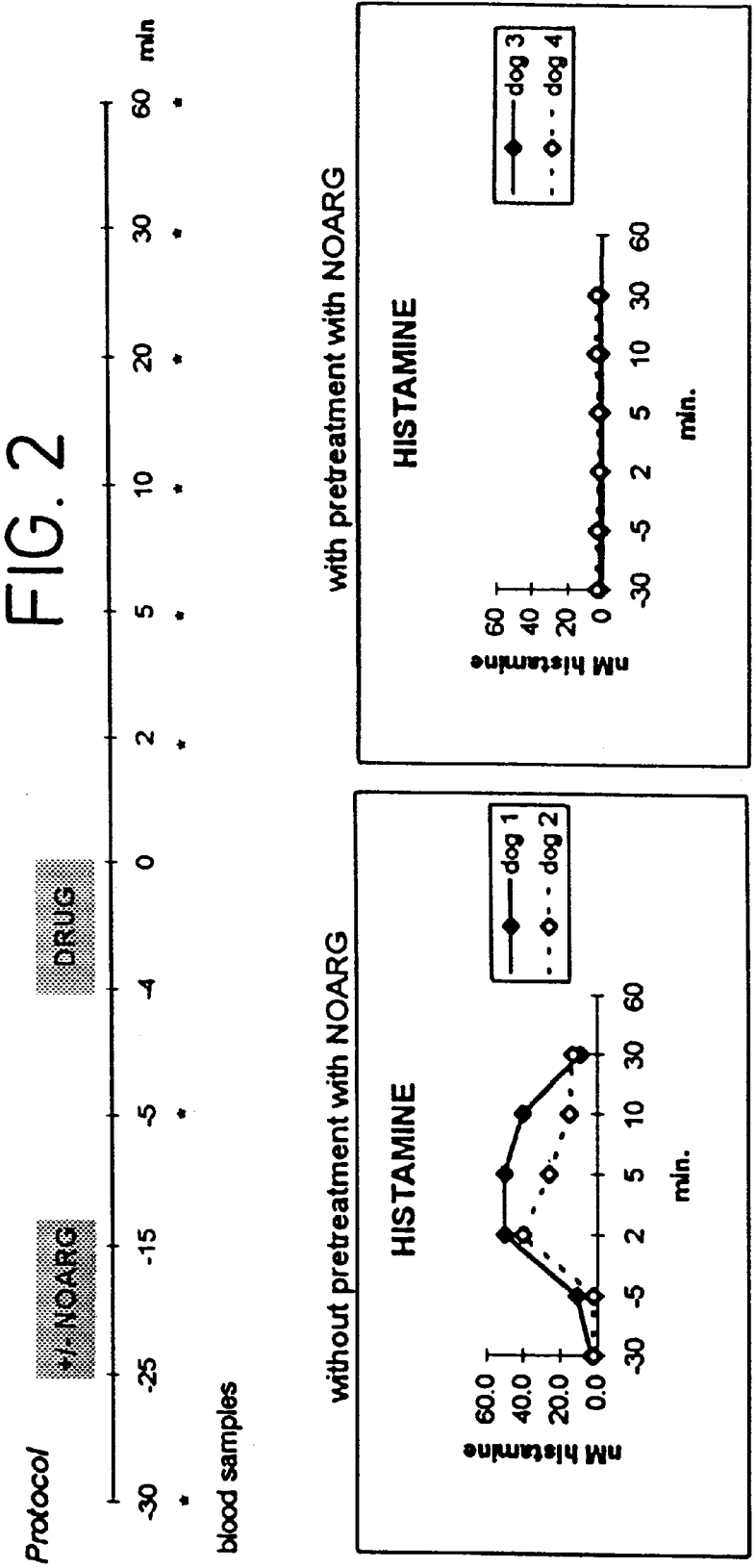

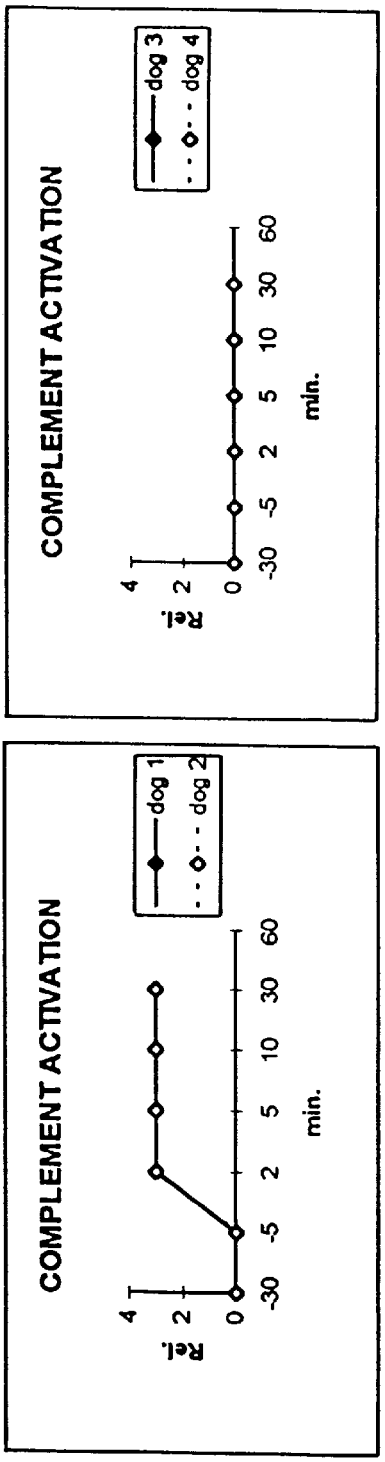
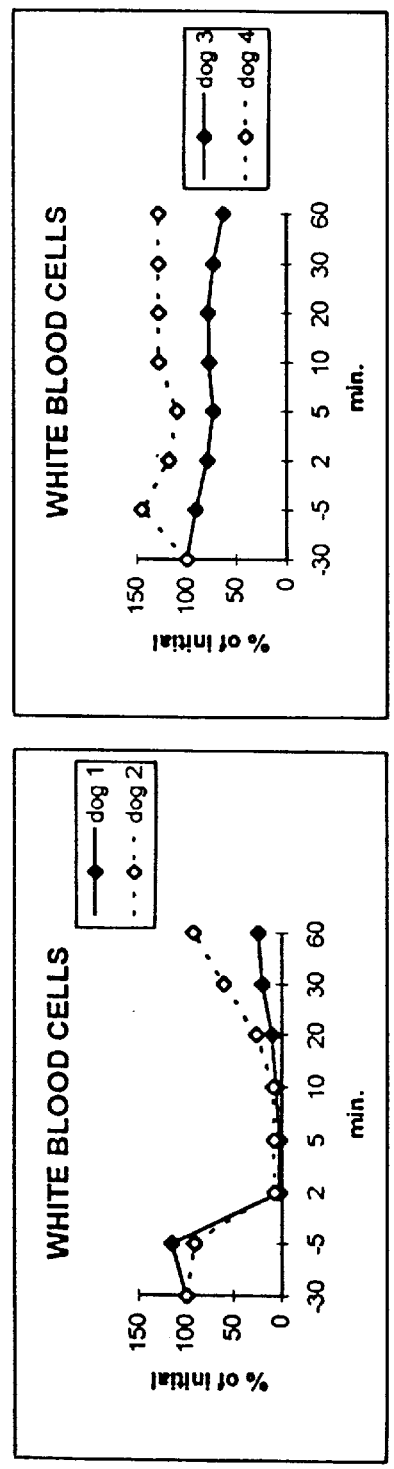
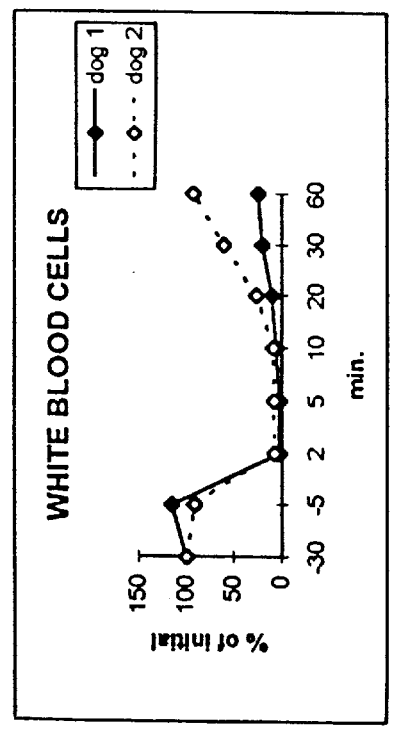
FIG. 2(c)  FIG. 2(d)  FIG. 2(e)  FIG. 2(f)

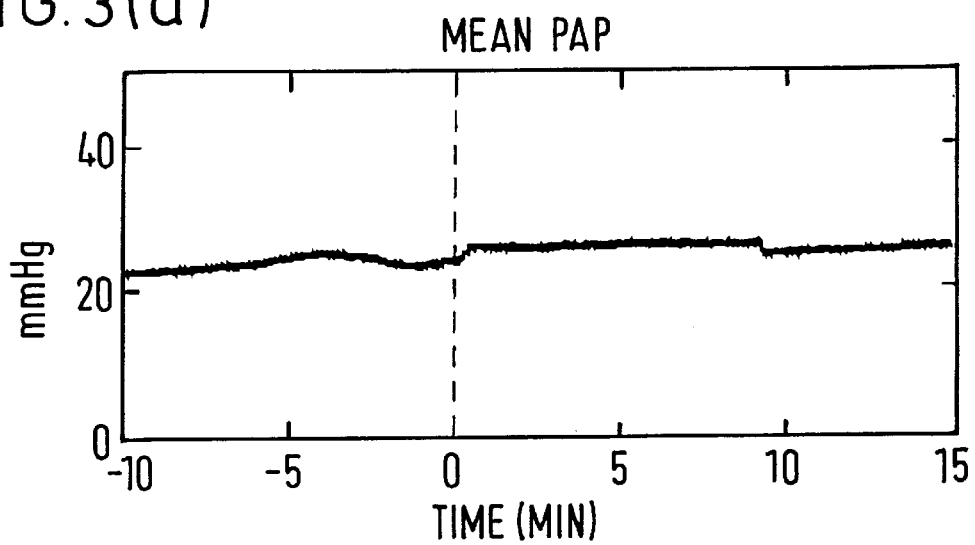
FIG. 3(a)
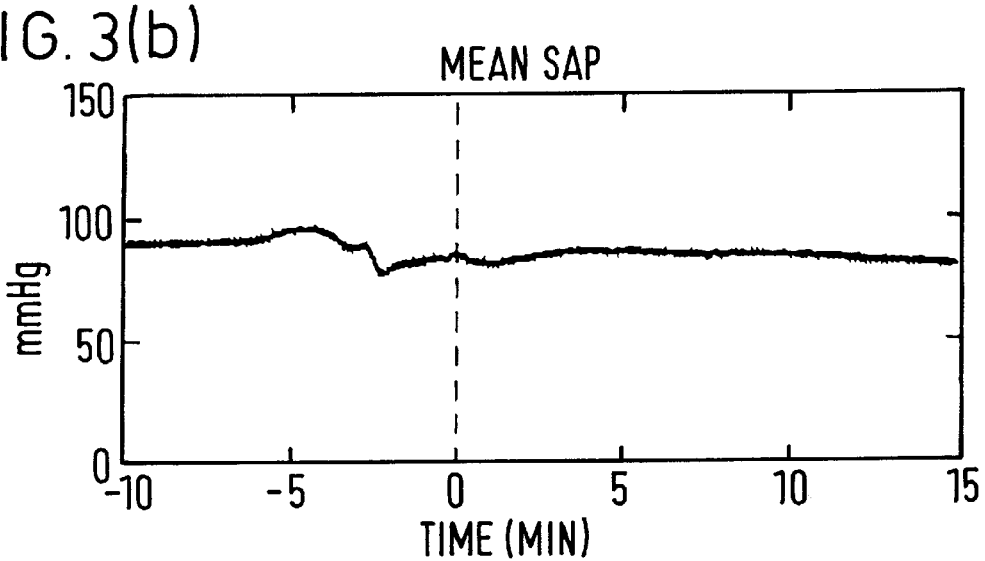
FIG. 3(b)
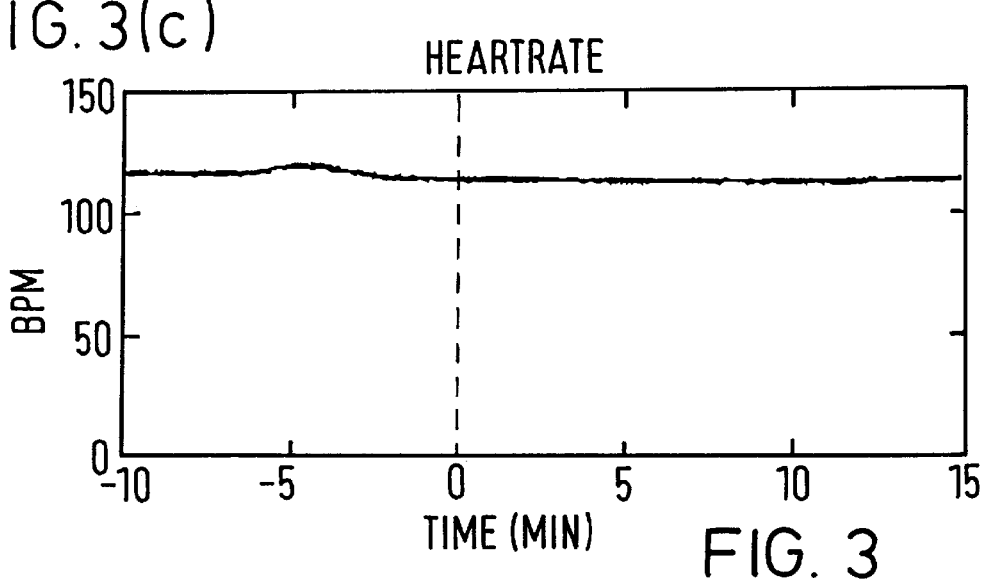
FIG. 3(c)
FIG. 3

USE OF NITRIC OXIDE INHIBITORS FOR TREATING SIDE EFFECTS OF PARTICULATE DRUGS

This application is a continuation of pending international application number PCT/GB97/03239 filed Nov. 26, 1997 benefit of which is hereby claimed (of which the entire disclosure of the pending, prior application is hereby incorporated by reference), which itself is a continuation-in-part of U.S. provisional application No. 60/046,647 filed May 16, 1997.

This invention relates to the use of nitric oxide synthetase inhibitors and nitric oxide antagonists (herein collectively referred to as NOSIs) in conjunction with parenteral particulate pharmaceutical agents, and to pharmaceutical compositions comprising NOSIs.

It has long been known that parenteral administration of particulate pharmaceutical agents, in particular injection of such agents into the vasculature, may cause unwanted physiological effects. As a result the development of particulate parenteral pharmaceutical compositions has faced problems not encountered in the development of parenteral compositions containing water-soluble drug substances in solution.

Examples of the unwanted physiological effects encountered with parenteral administration of particulate materials include changes in systemic blood pressure, elevated pulmonary arterial pressure, reduced cardiac output, reduced perfusion of liver and intestines, acute thrombocytopenia, acute neutrocytopenia, release of histamine, thromboxane, platelet activating factor and tumor necrosis factor, complement activation including formation of anaphylatoxins such as C3a and C5a, and activation of the blood clotting system, Hageman factor and bradykinin system. Moreover many examples of release of mediators from phagocytic cells (such as Kupffer cells) and vascular endothelium have been noted as have many other effects related to activation of the body's defense systems against foreign materials.

The particulate materials which provoke such unwanted physiological effects may take many very different forms, eg. lipid emulsions, liposome and micelle drug formulations (including therapeutic or diagnostic agents), solid particles (such as polymer microspheres, carbohydrate (eg. starch) microspheres and protein (eg. albumin) microspheres), colloids, lipophilic emulsions and gaseous microbubbles. The common factor for such agents is their particulate nature.

Particular examples of particulate agents which provoke unwanted effects include liposomes, either empty or encapsulating Amphotericin-B or iodinated water-soluble X-ray contrast agents, and lipophilic drug emulsions of drugs such as a Taxol (paclitaxel), cyclosporin, althesin, propanidide, vitamin K, Amphotericin-B, diazepam and other lipophilic drugs. Such formulations commonly employ Cremophor-EL as an emulsifier and it has been found that even drug-free emulsions of Cremophor-EL provoke such unwanted physiological effects.

In view of the widely differing chemical/physical natures of such particulate agents, it has until now been considered that the unwanted effects result from a wide variety of reactions relating to the surface properties of the particles and their interaction with humoral and cellular defense mechanisms. In agreement with this multifactorial hypothesis, no unitary pharmacological treatment has been developed to combat the unwanted physiological effects of parenteral particulate administration. Most commonly, therapy to counter such effects has involved administration of a combination of corticosteroids, histamine H1 and H2 receptor antagonists, and indomethacin or other NSAIDs. Such treatments have been based upon the assumption that the mechanism responsible for the unwanted effects is immunological, allergic, pseudoallergic, anaphylactic or anaphylactoid in nature.

Although efforts have been made to reduce the unwanted effects by modification of the surface properties of the particles, eg. by providing a negative surface charge, or by incorporation of carboxylic acids or polyethylene glycols, avoidance of the unwanted effects has been difficult to achieve.

The present invention is based upon the surprising finding that treatment of the subject receiving the parenteral particulate agent with NOSIs can completely eliminate certain of the most severe unwanted effects and may significantly reduce other unwanted effects.

A BRIEF DESCRIPTION OF THE DRAWINGS

FIG. 1 shows a plot demonstrating the protocol of Example 1 (see below), indicating the times at which the cardiovascular parameters were measured, and the times of injection of cardiovascular drug;

FIG. 1(a) is a plot (pressure (MSAP)v times) showing the cardiovascular response of dog 1 and dog 2 to an injection of the liposomal drug without pre-treatment with NOARG;

FIG. 1(b) is a plot (pressure MSAP)v time) showing the cardiovascular response of dog 3 and dog 4 to an injection of the liposomal drug with pre-treatment with NOARG;

FIG. 1(g) is a plot (pressure (PF)v time) showing the cardiovascular response of dog 1 and dog 2 to an injection of the liposomal drug without pre-treatment with NOARG;

FIG. 1(h) is a plot (pressure (PF)v time) showing the cardiovascular response of dog 3 and dog 4 to an injection of the liposomal drug with pre-treatment with NOARG;

FIG. 2 shows a plot demonstrating the protocol of Example 1 (see below), indicating the times at which the cardiovascular parameters were measured, and the times of injection of cardiovascular drug;

FIG. 2(a) is aplot (nM histamine v Time) showing change in histamine in dog 1 and dog 2 after injection of the liposomal drug without pre-treatment with NOARG;

FIG. 2(b) is a plot (nM histamine v time) showing change in histamine in dog 3 and dog 4 after injection of the liposomal drug with pre-treatment with NOARG;

FIG. 2(c) is a plot (Relative change in complement v time) showing change in complement activation in dog 1 and dog 2 after injection of the liposomal drug without pre-treatment with NOARG;

FIG. 2(d) is a plot (Relative change in complement v time) showing change in complement activation in dog 3 and dog 4 after injection of the liposomal drug with pre-treatment with NOARG;

FIG. 2(e) is a plot (Percentage of initial white blood cells v time) showing change in white blood cell count in dog 1 and dog 2 after injection of the liposomal drug without pre-treatment with NOARG;

FIG. 2(f) is a plot (Percentage of initial white blood cells v time) showing change in white blood cell count in dog 3 and dog 4 after injection of the liposomal drug with pre-treatment with NOARG;

FIG. 3(a) is a plot (pressure (PAP)v time) showing the cardiovascular response of a dog before and after injection of emulsion with pre-treatment of NOARG;

FIG. 3(b) is a plot (pressure (SAP)v time) showing the cardiovascular reponse of a dog before and after injection of emulsion with pre-treatment of NOARG;

FIG. 3(c) is a plot (heart rate v time) showing the cardiovascular response of a dog before and after injection of emulsion with pre-treatment of NOARG.

Figure 1C:
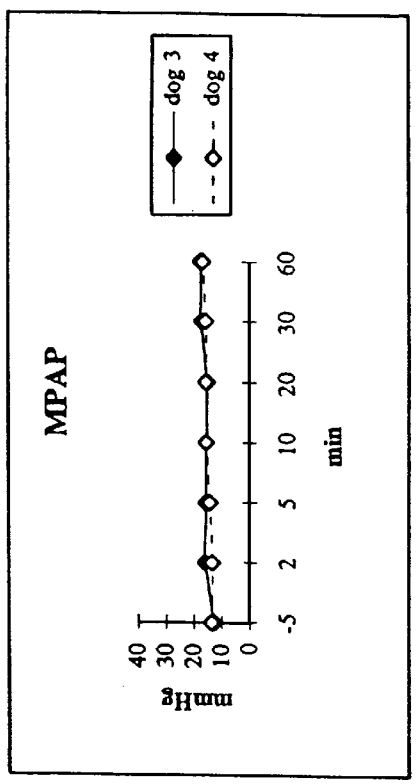
FIG. 1(c) is a plot (pressure (MPAP)v time) showing the cardiovascular response of dog 1 and dog 2 to an injection of the liposomal drug without pre-treatment with NOARG.
Figure 1D:
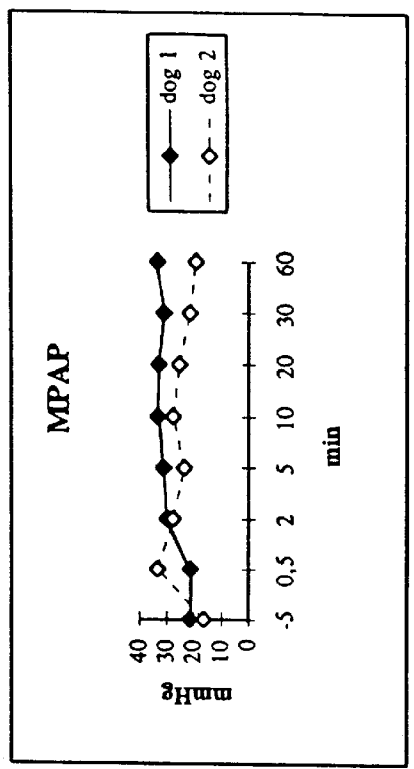
FIG. 1(d) is a plot (pressure (MPAP)v time) showing the cardiovasculat response of dog 3 and dog 4 to an injection of the liposomal drug with pre-treatment with NOARG.
Figure 1E:
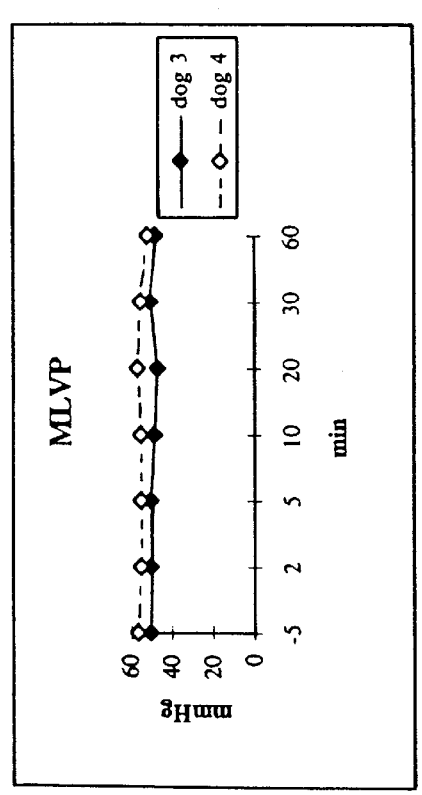
FIG. 1(e) is a plot (pressure (MLVP)v time) showing the cardiovascular response of dog 1 and dog 2 to an injection of the liposomal drug without pre-treatment with NOARG.
Figure 1F:
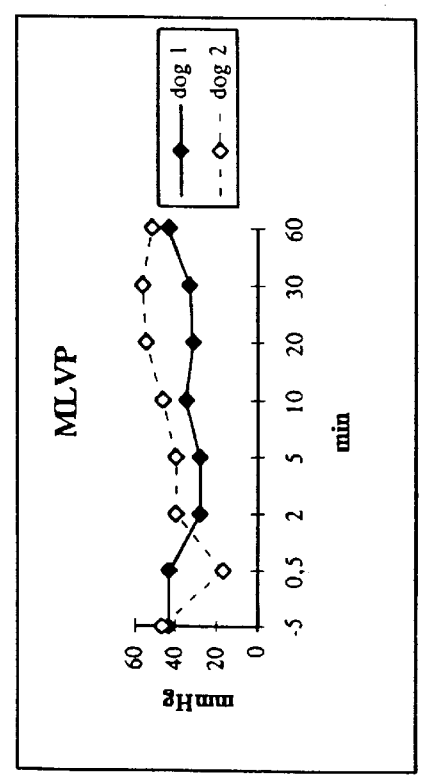
FIG. 1(f) is a plot (pressure (MLVP)v time) showing the cardiovascular response of dog 3 and dog 4 to an injection of the liposomal drug with pre-treatment with NOARG.

NOSI's have previously been proposed as agents for use in reducing unwanted physiological effects, eg. in cancer therapy as described in WO95/09621 (Wellcome Foundation), however no suggestion has been made that they may advantageously be used to prevent or reduce unwanted effects encountered with parenteral administration of particulate drug agents.

Thus view from one aspect the invention provides the use of a nitric oxide synthetase inhibitor or nitric oxide antagonist (ie. a NOSI) for the manufacture of a medicament for use in method of treatment of the human or non-human (preferably mammalian) body to combat unwanted physiological effects of parenteral administration of particulate drugs.

Veiwed from a further aspect the present invention provides a method of treatment of the human or non-human (preferably mammalian) body to combat unwanted physiological effects of parenteral administration of particulate drugs, said method comprising parenterally administering to said body a particulate drug (eg. a therapeutic, prophylactic or diagnostic agent) and previously, simultaneously or subsequently (preferably previously) administering to said body a side effect reducing amount of a NOSI.

Viewed from a still further aspect the invention also provides a pharmaceutical composition in a form adapted for parenteral administration (eg. a suspension or dispersion) comprising a particulate drug (eg. a therapeutic, prophylactic or diagnostic agent) and a NOSI, preferably together with at least one physiologically tolerable carrier or excipient.

Viewed from a yet further aspect the invention provides a kit comprising a first pharmaceutical composition in a form adapted for parenteral administration (eg. a suspension or dispersion) comprising a particulate drug (eg. a therapeutic, prophylactic or diagnostic agent) together with at least one physiologically tolerable carrier or excipient and a second pharmaceutical composition comprising a NOSI together with at least one physiologically tolerable carrier or excipient, optionally together with instructions for separate or simultaneous administration of said first and said second pharmaceutical compositions.

Many NOSIs are known and may be used in accordance with the present invention. Suitable examples include the L-arginine analogs N-ω-methyl-L-arginine (NMA) (synthesisable as described by Corbin et al., Anal. Biochem. 57: 310 (1974) and available from Sigma Chemical Co.), N-ω-nitro-L-arginine (NOARG, available from Sigma Chemical Co.), N-ω-nitro-L-arginine methyl ester (L-NAME —available from Sigma Chemical Co.), N-iminoethyl-L-ornithine (L-NIO), $N^G$-$N^G$-dimethylarginine (ADMA) and the equivalent D-analogs as well as other arginine and amidine analogs (eg. as described in U.S. Pat. No. 5,028,627 and WO93/13055), isothiourea derivatives as described in WO94/12165, physiologically tolerable redox agents such as methyl blue, arginine depleting agents such as arginase, arginine decarboxylase and arginine deaminase, and NO scavengers such as soluble transition metal complexes (eg. as described in WO94/26263). Further examples include arginine depleting agents, such as arginase, as described in U.S. Pat. No. 5,196,195.

Particularly preferably the NOSI used is a nitric oxide synthetase inhibitor, especially an L-arginine analog such as NMA, NOARG or L-NAME.

The NOSI may be administered together with, before, or after the particulate drug and may be formulated together with or separately from the particulate drug. Where the NOSI and the particulate drug are separately formulated, the NOSI may be formulated for administration by any conventional route, eg. oral, parenteral (eg. subcutaneous, intravenous, intraarterial, interstitial or intramuscular), rectal or topical. The compositions thus may conveniently be solutions, suspensions, emulsions, tablets, coated tablets, capsules, powders, syrups, sprays and suppositories.

Preferably, the NOSI will be formulated for separate administration, particularly preferably parenteral administration, and especially preferably for administration prior to (eg. up to 24 hours, preferably 5 minutes to 12 hours before) parenteral administration of the particulate agent. However due to the rapid onset of the protective effect of the NOSI (especially where it is administered parenterally), the NOSI can satisfactorily be administered only shortly before (eg. up to 5 minutes before), simultaneously with or shortly after (eg. up to 5 hours after) the particulate agent. If desired, further doses of NOSI can be given during the period from the initial NOSI administration up to 24 hours or even longer after the administration of the particulate drug. Formulations of the NOSI may contain conventional carriers and excipients, eg. saline, water for injection, buffers, osmolality adjusting agents, binders, lubricants, dispersants, inert diluents, etc. (eg. as described in WO95/09621).

Where the NOSI is administered topically, this can for example be sublingual, nasal, dermal or by aerosol inhalation. For dermal administration of charged NOSIs, electrophoretic administration techniques may be used.

Where the NOSI is formulated together with the particulate drug, it may be in the carrier medium (preferably an aqueous medium) or it may be in or on the drug particles, eg. bound to or adsorbed onto the particle surface or held within the particle, eg. in the core of a liposome or absorbed or incorporated into a solid particle core. Surface bound NOSI's may be bound via biodegradable linkages, eg. arginine analogs may be ester bound to bifunctional linker compounds (such as bifunctional polyalkylene oxides) which are themselves bound to the particle surface.

The dosage of the NOSI will depend upon the subject being treated, the dosage and nature of the particulate drug and the NO inhibiting power of the particular NOSI selected.

Generally however doses will be in the range 0.05 to 300 mg/kg body weight, eg. 0.5 to 100 mg/kg, preferably 1 to 10 mg/kg, eg. 80 mg to 0.8 g/day for an adult human of 80 kg. If the NOSI is administered intravenously or intraarterially, this will preferably be by bolus injection or infusion, eg. over a period of up to 30 minutes for example a period of 3 to 15 minutes, eg. up to 10 minutes, preferably up to 5 minutes. If the NOSI is orally, this may conveniently be in tablet form with single or multiple tablets being administered either in one dose or spread out over a period of time.

The particulate drug used according to the invention may be any parenterally administered particulate drug agent, eg. a therapeutic, prophylactic or diagnostic agent. The agent may for example be a solid particle, a gas microbubble, a water-miscible liquid droplet or a composite structure such as a gas or liquid containing liposome, vesicle or micelle. The particle may be and preferably will be surface modified to enhance biocompatibility or to modify biodistribution, eg. by provision of a surface charge, coating with a blood residence prolonging material or opsonization inhibitor (such as a polyalkylene oxide or a heparinoid), or by conjugation to a biotargetting vector.

Particularly preferably the particulate agent is a diagnostic agent, eg. a contrast agent effective in an imaging modality such as MR, X-ray, ultrasound, CT, scintigraphy, SPECT, PET, light imaging, EIT and magnetotomography (and other magnetometric imaging techniques).

Examples of suitable such diagnostic agents include gas microbubbles (either with or without an outer shell or membrane such as a liposomal membrane), mixtures of gas microbubbles and emulsions of volatile liquids, iodinated X-ray contrast agent containing liposomes, nanoparticulate insoluble x-ray contrast agents, paramagnetic metal chelate containing liposomes or zeolite particles, optionally surface coated superaparamagnetic metal oxide particles, and chromophore or fluorophore containing liposomes. Any biotolerable gas may be present in the gas microbubbles—the term gas in this respect is used to refer to a material which is gaseous or has a vapor pressure above 70 mmHg at 37° C. In compositions comprising mixtures of gas microbubbles and volatile liquids, the liquid should have a vapor pressure of at least 10 mmHg at 37° C. Examples of volatile liquids which may be used include but are not limited to perfluorocarbons eg. $C_{5-8}$ perfluorocarbons such as perfluoropentane, perfluorohexane, perfluoroheptane and perfluorooctane, and isomers thereof, eg. dimethylperfluorocyclobutane. Generally such particles will have mean diameters of up to 5 µm, preferably up to 1 µm. For gas microbubbles and gas filled vesicles (eg. micelles, liposomes and microballoons) the preferred diameter is in the range 3–5 µm, for vesicle drug formulations (eg. micelles or liposomes carrying therapeutic agents) the preferred diameter is in the range 0.2 to 0.5 µm and for solid cored particles the preferred range is 10 to 100 nm. Examples of such particulate contrast agents have been described in numerous patent publications, especially by Nycomed Imaging AS, Nycomed Salutar Inc., Sterling Winthrop Inc., Schering AG, Advanced Magnetics Inc., Meito Sangyo, Imarx, Bracco, Guerbet, Sonus and Alliance. In this regard reference may be had for example to WO93/05819 (Quay/Sonus), WO93/17718 (Nycomed), WO94/28780 (Unger/Imarx), WO95/01187 (MBI), WO92/22586 (Meito Sangyo), WO88/00060 (AMI) and GB-B-2185397 (Danbiosynt).

The particulate compositions will conveniently contain carriers and excipients such as water for injections, saline, buffers, antioxidants, dispersants, emulsifiers, osmolality adjusters and cryoprotectants.

The particulate compositions will conveniently contain an effective dose of the particulate drug, effective that is to produce the desired therapeutic, prophylactic or diagnostic effect. Dosages conventional for the particulate drug selected may be used. However with the reduction in unwanted physiological effects achieved according to the invention by the use of the NOSI, higher than conventional doses, eg. increases of 10% or more, maybe used thereby increasing the therapeutic, prophylactic or diagnostic efficacy that can be safely achieved.

Using a NOSI according to the invention, it has been surprisingly found that several of the most severe unwanted physiological effects of certain particulate drugs are completely avoided, eg. the severe changes in systemic blood pressure, pulmonary vascoconstriction, reduced myocardial contractility, histamine release, complement activation, and anaphylactoid collapse observed when NOSIs are not used. Moreover use of NOSIs was found to lead to major reductions in other unwanted physiological effects such as severe thrombocytopenia, neutrocytopenia, thromboxane production, reduced hepatic and splenic drug flow which otherwise are observed.

The patent and literature references referred to herein are hereby incorporated by reference.

Figure 2H:
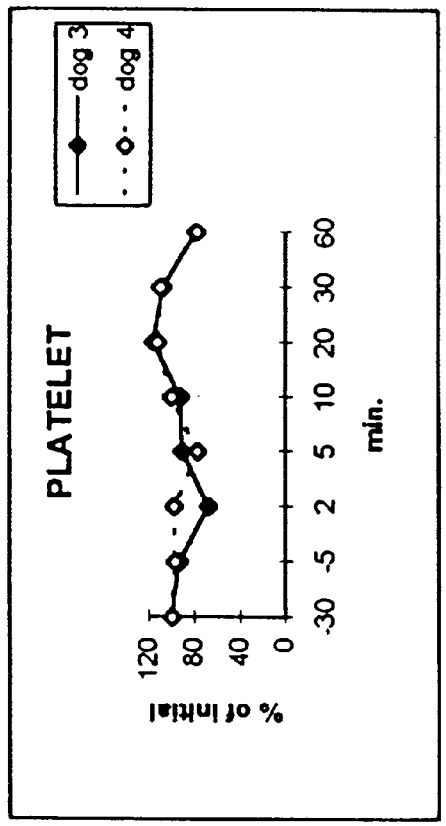
FIG. 2(h) is a plot (Percentage of initial platelet count v time) showing change in platelet count in dog 3 and dog 4 after injection of the liposomal drug without pre-treatment with NOARG.
Figure 2G:
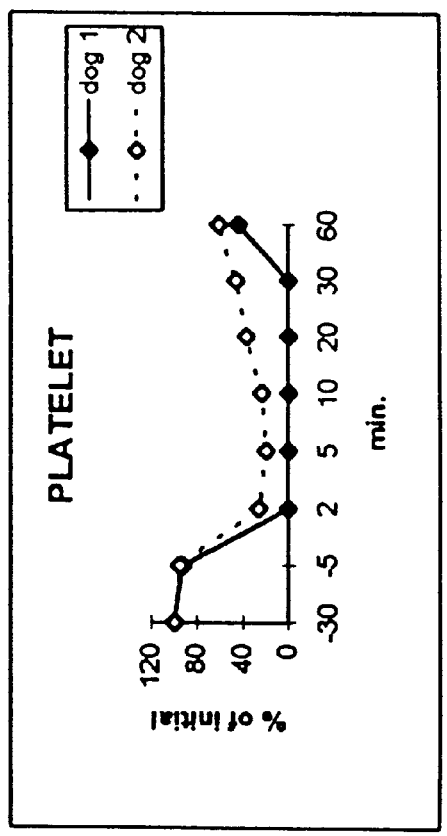
FIG. 2(g) is a plot (Percentage of initial platelet count v time) showing change in platelet count in dog 1 and dog 2 after injection of the liposomal drug without pre-treatment with NOARG.

The present invention will now be further illustrated by the following non-limiting Examples and the accompanying drawings in which:

FIG. 1 shows comparative plots of cardiovascular parameters for dogs without and with NOSI treatment according to the invention;

FIG. 2 shows comparative plots of blood parameters for dogs without and with NOSI treatment according to the invention; and FIG. 3 shows plots of cardiovascular parameters for a dog with NOSI treatment according to the invention.

EXAMPLE 1

Material

Particulate Drug Formulation:

A liposomal drug suitable for use as a CT contrast agent, consisting of phosphatidylcholine/phosphatidylserine in a 10:1 weight ratio as the membrane forming material and with iodixanol encapsulated within the liposomes. The concentration of encapsulated iodine was 80 mgI/ml of liposomal composition as a whole and the anticipated clinical dose was 100 mgI/kg. The composition may be made as described in WO95/26205.

Nitric Oxide Synthetase Inhibitor (NOSI):

N-ω-nitro-L-arginine (NOARG) from Sigma Chemical Co. (cat no. N-5501). A 10 mg/ml solution was prepared by adding 200 µl EN NaOH and 20 ml 0.9% saline to 200 mg NOARG. The solution was moderately heated (~37° C.) and hand shaken to achieve a clear solution. To sterilize, the solution was filtered through a 0.2 µm filter. The solution was stored overnight at 4° C. before use.

EXAMPLE 2

Dog Study 4 mongrel dogs (15–20 kg) were divided into two groups; one group received only the liposomal drug of Example 1 and the second group received pretreatment with NOARG prior to injection of the liposomal drug.

The animals were anaesthetized with 25 mg/kg pentobarbital i.v. maintained with 1–3 mg/kg/hour as needed, and ventilated with room air on a Large Animal Respirator. A Swann-Ganz catheter was placed in the pulmonary artery and a fluid filled catheter in a femoral artery to measure pulmonary arterial pressure (PAP) and systemic arterial pressure (SAP). Through the left vena carotis a Millar Catheter was placed in the left ventricle to measure left ventricular pressure (LVP). An electromagnetic flow probe was placed on the opposite femoral artery to monitor peripheral flow (PF). After surgery, the dogs were allowed to stabilize pressure, respiration and blood gases. A baseline blood sample was taken for hematology and mediator analysis (t=−30 min).

For group 1, 100 mgI/kg of the liposomal drug was infused at the rate of 6 ml/min resulting in an infusion period of about 4 min.

For group 2, 5 mg/kg NOARG was injected at the rate of 1 ml/min resulting in an infusion period of about 10 min. 10 min after finishing NOARG infusion, the liposomal drug was infused as described above. A blood sample (−5 min) was taken prior to liposomal drug infusion.

Cardiovascular parameters were continuously monitored and blood samples for hematology and mediator analysis were taken +2, +5, +10, +20, +30 and +60 min after finishing the liposomal drug infusion (as indicated by the protocol diagrams in FIGS. 1 and 2 of the accompanying drawings). The study was terminated by an overdose pentobarbital and potassium i.v.

The blood samples for hematology were analyzed on an automatic blood cell analyzer, Technicon H*1, on the day of blood sampling. For mediator analysis, plasma samples were prepared and stored at −70° C. for later analysis. Histamine was analyzed using a commercially available kit (Immunotech ref. no. 1153). The complement activation was analyzed by an immunoblotting technique using polyclonal antibodies against dog C3 split products (Organon art. no 55351).

FIGS. 1(a), to 1(h) of the accompanying drawings shows the cardiovascular response in 4 individual dogs after injection of the liposomal drug without and with pretreatment with NOARG (left and right column, respectively). Pressure changes are shown in mm Hg. Without pretreatment with NOARG, MSAP (mean systemic arterial pressure), FIG. 1(a) MPAP (mean pulmonary arterial pressure), FIG. 1(c) MVLP (mean left ventricular pressure) (FIG. 1(e)) and PF (peripheral flow) (FIG. 1(g)) were significantly affected. These cardiovascular effects were completely inhibited by use of NOARG FIGS. 1(b), 1(d), 1(f) and 1(h), respectively.

FIGS. 2(a) to 2(h) of the accompanying drawings shows the mediator release and hematological effects in 4 individual dogs after injection of the liposomal drug without and with pretreatment with NOARG (left and right column, respectively). Changes in histamine are shown in nM, change in complement activation is relative (Rel.), and changes in white blood cell and platelet counts are shown as a percentage of the initial value. Without pretreatment with NOARG a significant release of histamine (FIG. 2(a)), complement activation (FIG. 2(c)) and depletion of circulating white blood cells (FIG. 2(e)) and blood platelets (FIG 2(g)) were observed. All these effects were completely inhibited by use of NOARG FIGS. 2(b), 2(d), 2(f) and 2(h), respectively.

EXAMPLE 3

Dog Study 2 mongrel dogs with body weights of about 20 kg were used for evaluation of the ultrasound imaging effect of emulsions of volatile liquids, and mixtures of volatile liquids and gas microbubbles. One dog received a mixture of 1.5 microliter emulsion droplets per kg of dimethylperfluorocyclobutane and 0.2 microliter gas microbubbles per kg of perfluorobutane. The emulsion and gas microbubbles were both stabilized with hydrated egg phosphatidylserine, and the median droplet size of the emulsion and the median size of the gas microbubbles were both 3 micrometers. Imaging of the heart was done with an ATL HDI3000 scanner in fundamental B-mode at high power output. The emulsion and gas suspension were injected simultaneously at a rate of 1 ml/sec.

Within one minute after injection, the dog developed a severe cardiovascular response with a dramatic drop in systemic blood pressure, and elevated pulmonary arterial pressure similar to the responses shown in FIG. 1.

In order to test if the response to this formulation was caused by the unwanted effects of nitric oxide, the other dog was pretreated with 5 mg/kg NOARG at a rate of 10 mg/min. Five minutes after completion of the NOARG infusion, the same mixture of perfluorobutane microbubbles and dimethylperfluorocyclobutane was injected in the same way and in the same amounts as to the first dog. The unwanted cardiovascular response to the formulation was essentially abolished as is demonstrated by the MPAP, MSAP and heart rate plots shown in FIGS. 3(a), 3(b), and 3(c), respectively of the accompanying drawings.

What is claimed is:

1. A method of reducing adverse physiological effects due to parenteral administration of particulate drugs in a patient in need thereof comprising administering to said patient a therapeutically effective amount of a nitric oxide synthetase inhibitor or nitric oxide antagonist.

2. The method of claim 1 wherein said nitric oxide synthetase inhibitor or nitric oxide antagonist is a nitric oxide synthetase inhibitor.

3. The method of claim 2 wherein said nitric oxide synthetase inhibitor is an L-arginine analog.

4. The method of claim 2 wherein said nitric oxide synthetase inhibitor or nitric oxide antagonist is N-ω-nitro-L-arginine.

5. The method of claim 1 wherein said particulate drug is a diagnostic imaging contrast agent composition.

6. The method as claimed in claim 5 wherein said composition is an echogenic contrast agent for ultrasound imaging.

7. The method as claimed in claim 5 wherein said composition is an X-ray contrast medium.

8. The method of claim 1 wherein said particulate drug is a composition comprising gas microbubbles, an emulsion containing droplets of a volatile liquid or a mixture thereof.

9. A pharmaceutical composition in a form adapted for parenteral administration comprising a particulate drug and a nitric oxide synthetase inhibitor or nitric oxide antaonist.

10. A kit comprising a first pharmaceutical composition in a form adapted for parenteral administration comprising a particulate drug together with at least one physiologically tolerable carrier or excipient and a second pharmaceutical composition comprising a nitric oxide synthetase inhibitor or nitric oxide antagonist together with at least one physiologically tolerable carrier or excipient, optionally together with instructions for separate or simultaneous administration of said first and said second pharmaceutical compositions.

11. A kit as claimed in claim 10, wherein said particulate drugs is a diagnostic imaging contrast agent composition.

12. A kit as claimed in claim 11, wherein said nitric oxide synthetase inhibitor or nitric oxide antagonist is an L-arginine analog.

13. A method of reducing adverse physiological effects due to parenteral administration of a particulate drug in a patient in need thereof, said method comprising parenterally administering to said patient a particulate drug and previously, simultaneously or subsequently administering to said patient a side-effect reducing amount of a nitric oxide synthetase inhibitor or nitric oxide antagonist.

14. A method as claimed in claim 13, wherein said nitric oxide synthetase inhibitor or nitric oxide antagonist is an L-arginine analog and particulate drug is a diagnostic imaging contrast agent composition.

15. A method as claimed in claim 14, wherein said nitric oxide synthetase inhibitor or nitric oxide antagonist is N-ω-nitro-L-arginine.

16. A method as claimed in claim 14, wherein said composition is an echogenic contrast agent for ultrasound imaging or an X-ray contrast medium.

17. A method as claimed in claim 15, wherein said particulate drug is a composition comprising gas microbubbles, an emulsion containing droplets of a volatile liquid or a mixture thereof.

18. A composition as claimed in claim 9, wherein said nitric oxide synthetase inhibitor or nitric oxide antagonist is an L-arginine analog and the particulate drug is a diagnostic imaging contrast agent composition.

19. A composition as claimed in claim 9, wherein said nitric oxide synthetase inhibitor or nitric oxide antagonist is or N-ω-nitro-L-arginine.

20. A composition as claimed in claim 18, wherein said particulate drug composition is an echogenic contrast agent-for ultrasound imaging or an X-ray contrast medium.

21. A composition as claimed in claim 20, wherein said particulate drug is a composition comprising gas microbubbles, an emulsion containing droplets of a volatile liquid or a mixture thereof.

* * * * *